United States Patent
McKee et al.

(10) Patent No.: US 9,285,359 B2
(45) Date of Patent: Mar. 15, 2016

(54) PROTEIN DETECTION USING MODIFIED CYCLODEXTRINS

(71) Applicant: Bio-Rad Laboratories, Inc., Hercules, CA (US)

(72) Inventors: Clayton T. McKee, Davis, CA (US); William Strong, El Cerrito, CA (US); Lee Olech, Pinole, CA (US); Thomas Berkelman, Oakland, CA (US); Christopher Belisle, Walnut Creek, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 14/455,609

(22) Filed: Aug. 8, 2014

(65) Prior Publication Data

US 2015/0044705 A1 Feb. 12, 2015

Related U.S. Application Data

(60) Provisional application No. 61/864,388, filed on Aug. 9, 2013.

(51) Int. Cl.
*G01N 33/53* (2006.01)
*G01N 33/58* (2006.01)
(Continued)

(52) U.S. Cl.
CPC .......... *G01N 33/5306* (2013.01); *G01N 33/582* (2013.01); *G01N 33/6803* (2013.01); *G01N 27/44747* (2013.01); *G01N 2400/18* (2013.01)

(58) Field of Classification Search
None
See application file for complete search history.

(56) References Cited

U.S. PATENT DOCUMENTS

| 6,858,723 B1 | 2/2005 | Auzely-Velty et al. |
| 7,569,130 B2 | 8/2009 | Edwards et al. |

(Continued)

FOREIGN PATENT DOCUMENTS

| WO | 91/05605 A1 | 5/1991 |
| WO | 2006/037930 A1 | 4/2006 |
| WO | 2013/027008 A1 | 2/2013 |

OTHER PUBLICATIONS

Djedaïni-Pilard et al.; "Potential formation of intramolecular inclusion complexes in peptidocyclodextrins as evidenced by NMR spectroscopy"; *J. Chem. Soc. Perkin Transl.*; 2:723-730 (1995).

(Continued)

*Primary Examiner* — Jacob Cheu
(74) *Attorney, Agent, or Firm* — Kilpatrick Townsend & Stockton LLP

(57) ABSTRACT

A method is provided for detecting a protein using a cyclodextrin covalently linked to at least one label. The cyclodextrin can associate with the protein by sequestering an aromatic amino acid side-chain of the protein in its hydrophobic cavity. After contacting the protein with the cyclodextrin, the label can be detected directly or can undergo a chemical interaction with a reagent to form a detectable product. The label can include an indole moiety, which can react with a halo-substituted organic compound upon exposure to UV light and thereby be rendered fluorescent. Alternatively, the label can include a biotin moiety, which can bind to a binding partner such as avidin, or variants thereof, to form a detectable molecular complex. A labeled cyclodextrin can be used in the present methods to detect a protein of interest in an electrophoresis gel or on a blotting membrane. Aromatic amino acid residues of the protein, in particular tryptophan, remain protected from chemical modification due to sequestration by the cyclodextrin, making these methods compatible with downstream applications that require intact protein. Also provided herein are compositions, kits, and electrophoresis gels for use in detecting proteins.

20 Claims, 4 Drawing Sheets

(51) Int. Cl.
*G01N 33/68* (2006.01)
*G01N 27/447* (2006.01)

(56) References Cited

U.S. PATENT DOCUMENTS

| | | |
|---|---|---|
| 8,007,646 B2 | 8/2011 | Edwards et al. |
| 2003/0032043 A1 | 2/2003 | Pohl et al. |
| 2010/0089753 A1 | 4/2010 | Edwards et al. |

OTHER PUBLICATIONS

Djedaïni-Pilard et al.; "Synthesis-of a New Molecular Carrier: N-(Leu-enkephalin)yl 6-amido-6-deoxy-Cyclomaltoheptaose"; *Tetrahedron Letters*; 34(15):2457-2460 (1993).

Edwards et al.; "The light-induced reactions of tryptophan with halocompounds"; *Photochem. & Photobiol.*; 75:362-368 (2002).

Koushik et al.; "Interaction of [D-Trp6, Des-Gly10] LHRH Ethylamide and Hydroxy Propyl β-Cyclodextrin (HP β CD): THermodynamics of Interaction and Protection from Degradation by α-Chymotrypsin"; *Pharmaceutical Development and Technology*; 6(4):595-606 (2001).

Ladner et al.; "Visible fluorescent detection of proteins in polyacrylamide gels without staining"; *Analytical Biochemistry*; 326:13-20 (2004).

Ladner et al.; "Development of indole chemistry to label tryptophan residues in protein for determination of tryptophan surface accessibility"; *Protein Sci.*; 16:1204-1213 (2007).

Martin Del Valle, E.M.; "Cyclodextrins and their uses: a review"; *Process Biochemistry*; 39(9):1033-1046 (2004) *ePub* Oct. 2, 2003.

Rajgariah et al.; "Scope of amino acid recognition by cucurbit[8]uril"; *J. Incl. Phenom. Macrocycl. Chem.*; 62:251-254 (2008).

Schmidt et al., "Molecular interaction between the Strep-tag affinity peptide and its cognate target, streptavidin"; *J. Mol. Biol.*; 255:753-766 (1996).

Schneider et al.; "Selectivity in supramolecular host-guest complexes"; *Chem. Soc. Rev.*; 37:263-277 (2008).

Serno, et al.; "Protein stabilization by cyclodextrins in the liquid and dried state"; *Advanced Drug Delivery Reviews*; 63:1086-1106 (2011).

The International Search Report and Written Opinion from International Application No. PCT/US2014/050402, dated Dec. 16, 2014.

FIG. 2

Constant TCE = 0.5%v/v

NO MBCD    2.5mM MBCD    25mM MBCD

PROTEIN DETECTION USING MODIFIED CYCLODEXTRINS

CROSS-REFERENCES TO RELATED APPLICATIONS

The present application claims priority to U.S. Provisional Application No. 61/864,388, entitled "PROTEIN DETECTION USING MODIFIED CYCLODEXTRINS" and filed Aug. 9, 2013, the entire contents of which are incorporated herein by reference for all purposes.

BACKGROUND OF THE INVENTION

Many modern treatments for human diseases employ or target proteins. To develop such treatments, physicians and scientists require knowledge of the amino acid sequences, structures, and abundances of proteins that are expressed in the human body in various contexts, as well as interactions among these proteins. A key aspect of studying and manipulating proteins is detection. Proteins can be detected in vivo or in vitro, for purposes of analyzing or preparing protein samples, using a variety of techniques. Many of these techniques involve contacting proteins with a detectable binding partner.

Detection of proteins in electrophoresis gels is frequently performed using colored or fluorescent protein stains such as Coomassie Brilliant Blue or SYPRO Ruby. These stains can bind to proteins non-covalently, in a manner that is largely independent of amino acid sequence, and can be visualized upon illumination with specific wavelengths of light. Protein stains allow robust and sensitive detection, but hinder the rapid processing of biological samples for downstream applications. The process of applying the stain to the gel (staining) prior to detection can take hours. Similarly time consuming is the removal of the stain after detection (destaining), which can be necessary in order to obtain purified proteins when the gel is used preparatively. Staining and destaining involve agitation of the gel, prolonged immersion of the gel in an aqueous buffer, and frequent changes of this buffer. During these processes, some proteins (particularly low-molecular-weight and hydrophilic proteins) can diffuse out of the gel and into the buffer, thereby becoming lost to subsequent analysis. Use of protein stains, and the accompanying gel handling, can therefore reduce the number of proteins that can be identified after electrophoresis.

Alternatively, proteins can be made detectable by contacting the proteins with a halo-substituted organic compound and exposing the proteins to UV light. As disclosed by Edwards et al. in U.S. Pat. No. 7,569,103 B2 (Aug. 4, 2009) and U.S. Pat. No. 8,007,646 B2 (Aug. 30, 2011), and elsewhere, this procedure causes a UV-induced reaction between the indole moiety of tryptophan and the halo-substituted organic compound. Reacted tryptophan residues are covalently modified and fluorescent, undergoing excitation at the same wavelengths used to induce the reaction and emitting in the visible range. The reaction, and the associated reagents, apparatus, and methods used to perform the reaction and detect products thereof, are sometimes referred to by the name 'Stain-Free™' (Bio-Rad).

Proteins can be contacted with a halo-substituted organic compound and reacted before or after gel electrophoresis. Contact can also occur during electrophoresis in situ if the halo-substituted organic compound is a constituent of the gel. Detection of proteins using covalently modified tryptophan fluorescence, compared with using protein stains, is often more convenient and economical, and is also not limited to applications involving electrophoresis gels. For example, proteins can be contacted with the halo-substituted organic compound, reacted, and detected while suspended in solution or deposited on a blotting membrane.

Tryptophan and other aromatic amino acid side-chains can be protected from covalent modification by binding non-covalently to cyclodextrins, which are reviewed by Del Valle (E. M. M. Del Valle, *Process Biochemistry* 39, 1033-1046, 2004) and Serno et al. (T. Serno et al., *Advanced Drug Delivery Reviews* 63, 1086-1106, 2011). Cyclodextrins are cyclic oligosaccharides that include several (typically 6, 7, or 8) glucopyranose units joined by $\alpha$-(1,4) bonds. In a cyclodextrin molecule, the glucopyranose units form a tapered annular structure with a hydrophobic cavity at the center. Upon contact with a cyclodextrin, an aromatic amino acid side-chain can be inserted into the cavity, thereby becoming sequestered from further chemical interactions. Cyclodextrins have been used for example as excipients in protein-based drugs, and can prevent protein aggregation by limiting protein-protein interactions involving aromatic amino acids.

In addition to the standard $\alpha$-, $\beta$-, and $\gamma$-cyclodextrins, varieties of cyclodextrins with substituted glucopyranose units have been characterized. The substituents, in most cases attached at the 2, 3, and 6 positions, include alkyl, hydroxyalkyl, and carboxyalkyl groups. Cyclodextrins covalently linked to one or more amino acids have also been synthesized (see, for example, Djedaïni-Pilard et al., *J. Chem. Soc. Perkin Trans.* 2, 723-730, 1995).

Cyclodextrins are one class of cyclic organic molecules that can non-covalently bind smaller molecules to form supramolecular complexes. Such a cyclic molecule serves as the 'host' in host-guest chemistry (reviewed, for example, by H.-J. Schneider and A. K. Yatsimirsky in *Chem. Soc. Rev.*, 37, 263-277, 2008), and contains a central cavity to accommodate one or more appropriately sized 'guest' molecules through hydrogen bonding, ionic bonding, Van der Waals interactions, and/or hydrophobic interactions. The cyclic molecule can be an oligomer or polymer of repeating units, and can be referred to as a macrocycle. Other examples of cyclic organic host molecules include cucurbiturils, which are comprised of glycoluril monomers linked by methylene bridges. Cucurbit[8]uril has been shown to bind methyl viologen with 1:1 stoichiometry, and simultaneously accommodate methyl viologen and an amino acid in its cavity. Further, cucurbit[8]uril demonstrates binding specificity for the aromatic amino acids tryptophan, tyrosine, and phenylalanine (see P. Rajgariah and A. R. Urbach, *J. Incl. Phenom. Macrocycl. Chem.* 62, 251-254, 2008). Still other cyclic organic host molecules include pillararenes, calixarenes, and crown ethers.

SUMMARY OF THE INVENTION

Provided herein are methods, compositions, electrophoresis gels, and kits.

A method of detecting a protein is provided. The method includes contacting the protein with a cyclodextrin covalently linked to at least one label; contacting the protein with a reagent; causing the reagent to undergo a chemical interaction with the at least one label to form a product; and detecting the product, thereby detecting the protein.

In one embodiment of the method, the cyclodextrin is $\alpha$-cyclodextrin, $\beta$-cyclodextrin, methyl-$\beta$-cyclodextrin, or $\gamma$-cyclodextrin. In another embodiment, the at least one label is covalently linked to one or more glucopyranose units at the 6 position(s). In still another embodiment, the average number of labels per cyclodextrin is at least 1, 2, 3, 4, 5, 6, 7, 8, 12, 14, 16, 18, 21, or 24.

In some embodiments of the method, the at least one label includes an indole moiety. In some of these embodiments, the at least one label includes a tryptophan residue or a polypeptide. In other embodiments where the label includes an indole moiety, the at least one label does not include a tryptophan residue.

In some embodiments of the method, the reagent is a halo-substituted organic compound. In one such embodiment, the halo-substituted organic compound is chloroform, trichloroethanol, trichloroacetate, or 3-bromo-1-propanol.

In some embodiments, the causing step of the method involves exposing the protein to UV light and the product includes a substituted indole moiety. In one such embodiment, the substituted indole moiety differs in molecular weight from an unsubstituted indole moiety by 28, 44, or 58 Da. In another such embodiment, the substituted indole moiety includes a formyl, carboxylic acid, hydroxyethanone, or propanol group.

In some embodiments of the method, detecting the product includes detecting emitted light.

In some embodiments of the method, the at least one label includes a biotin moiety. In some embodiments, the reagent includes one of the following proteins: avidin, streptavidin, and neutravidin. In some embodiments, the chemical interaction is a binding interaction and the product is a non-covalent molecular complex of biotin and the reagent.

In some embodiments, the method further includes the step of subjecting the protein to gel electrophoresis, and the protein is detected in an electrophoresis gel. In some of these embodiments, the protein is contacted with the cyclodextrin and the reagent prior to gel electrophoresis. In one such embodiment, the cyclodextrin and reagent are suspended in a buffer and the contacting step includes contacting the protein with the buffer. In other embodiments, the protein is contacted with the cyclodextrin and the reagent subsequent to gel electrophoresis. In one of these other embodiments, the cyclodextrin and reagent are suspended in a buffer and the electrophoresis gel is contacted with said buffer, thereby allowing the cyclodextrin and reagent to diffuse into the electrophoresis gel and contacting the protein with the cyclodextrin and reagent. In still other embodiments, the cyclodextrin or reagent is a constituent of the electrophoresis gel, and the protein is contacted with the cyclodextrin or the reagent upon subjecting the protein to gel electrophoresis.

After subjecting the protein to gel electrophoresis, the method can include transferring the protein out of the electrophoresis gel and onto a blotting membrane, and detecting the protein on the blotting membrane. One embodiment of this method also includes removing the cyclodextrin, reagent, or product from the protein. In other embodiments of the method, the protein includes an affinity tag or antibody-binding epitope, and detecting the protein on the blotting membrane includes contacting the blotting membrane with a binding partner of the affinity tag or antibody-binding epitope. The affinity tag or antibody-binding epitope can include a tryptophan residue, and in one such embodiment, the affinity tag is a Strep-tag.

Also provided herein is a composition including: a cyclodextrin covalently linked to at least one label; and a reagent that undergoes a chemical interaction with the at least one label, thereby rendering the label detectable.

In one embodiment of the composition, the cyclodextrin is α-cyclodextrin, β-cyclodextrin, methyl-β-cyclodextrin, or γ-cyclodextrin. In another embodiment, the at least one label is covalently linked to one or more glucopyranose units at the 6 position(s).

In some embodiments of the composition, the at least one label includes an indole moiety. In some of these embodiments, the at least one label includes a tryptophan residue or a polypeptide. In other embodiments where the at least one label includes an indole moiety, the at least one label does not include a tryptophan residue.

In some embodiments, the reagent of the composition is a halo-substituted organic compound. In one such embodiment, the halo-substituted organic compound is chloroform, trichloroethanol, trichloroacetate, or 3-bromo-1-propanol.

In some embodiments of the composition, the at least one label includes a biotin moiety. In some embodiments, the reagent includes one of the following proteins: avidin, streptavidin, and neutravidin.

In other embodiments of the composition, the average number of labels per cyclodextrin is at least 1, 2, 3, 4, 5, 6, 7, 8, 12, 14, 16, 18, 21, or 24.

An electrophoresis gel is also provided herein. In some embodiments, the electrophoresis gel includes the composition described above.

In other embodiments, the electrophoresis gel includes a cyclodextrin covalently linked to at least one label. In one such embodiment, the cyclodextrin is α-cyclodextrin, β-cyclodextrin, methyl-β-cyclodextrin, or γ-cyclodextrin. In another such embodiment, the at least one label is covalently linked to one or more glucopyranose units at the 6 position(s).

In some embodiments of the electrophoresis gel, the at least one label includes an indole moiety. In some of these embodiments, the at least one label includes a tryptophan residue or a polypeptide. In other embodiments where the at least one label includes an indole moiety, the least one label does not include a tryptophan residue.

In some embodiments of the electrophoresis gel, the at least one label includes a biotin moiety.

In some embodiments of the electrophoresis gel, the average number of labels per cyclodextrin is at least 1, 2, 3, 4, 5, 6, 7, 8, 12, 14, 16, 18, 21, or 24.

Also provided herein is a kit. In some embodiments, the kit includes the composition described above. In some of these embodiments, the kit also includes an electrophoresis gel, where the composition is a constituent of the electrophoresis gel.

In some embodiments, the kit includes the electrophoresis gel described above.

In some embodiments, the kit includes a cyclodextrin covalently linked to at least one label, and a reagent that undergoes a chemical interaction with the at least one label, thereby rendering the label detectable. In one such embodiment, the cyclodextrin is α-cyclodextrin, β-cyclodextrin, methyl-β-cyclodextrin, or γ-cyclodextrin. In another such embodiment, the at least one label is covalently linked to one or more glucopyranose units at the 6 position(s).

In some embodiments of the kit, the at least one label includes an indole moiety. In some of these embodiments, the at least one label includes a tryptophan residue or a polypeptide.

In other embodiments where the at least one label includes an indole moiety, the at least one label does not include a tryptophan residue.

In some embodiments, the reagent of the kit is a halo-substituted organic compound. In one such embodiment, the halo-substituted organic compound is chloroform, trichloroethanol, trichloroacetate, or 3-bromo-1-propanol.

In some embodiments of the kit, the at least one label includes a biotin moiety. In some embodiments, the reagent includes one of the following proteins: avidin, streptavidin, and neutravidin.

In some embodiments of the kit, the average number of labels per cyclodextrin is at least 1, 2, 3, 4, 5, 6, 7, 8, 12, 14, 16, 18, 21, or 24.

Where the kit includes a cyclodextrin and a reagent, in some embodiments the kit also includes an electrophoresis gel of which the cyclodextrin is a constituent. In other embodiments, the kit also includes an electrophoresis gel of which the reagent is a constituent. In one such embodiment, the cyclodextrin is also a constituent of the electrophoresis gel.

Where the kit includes a cyclodextrin and a reagent, in some embodiments the kit also includes an aqueous buffer of which the cyclodextrin is a constituent. In one such embodiment, the aqueous buffer is Laemmli buffer.

Further provided is a composition including a cyclodextrin covalently linked to at least one substituted indole moiety. In one embodiment of the composition, the cyclodextrin is α-cyclodextrin, β-cyclodextrin, methyl-β-cyclodextrin, or γ-cyclodextrin. In another embodiment, the at least one substituted indole moiety is covalently linked to one or more glucopyranose units at the 6 position(s). In yet another embodiment, the substituted indole moiety differs in molecular weight from an unsubstituted indole moiety by 28, 44, or 58 Da. In still another embodiment, the substituted indole moiety includes a formyl, carboxylic acid, hydroxyethanone, or propanol group. In other embodiments, the substituted indole moiety is the product of a UV-induced reaction of an unsubstituted indole moiety with a halo-substituted organic compound. In one such other embodiment, the halo-substituted organic compound is chloroform, trichloroethanol, trichloroacetate, or 3-bromo-1-propanol. In yet another embodiment of the composition, the average number of substituted indole moieties per cyclodextrin is at least 1, 2, 3, 4, 5, 6, 7, 8, 12, 14, 16, 18, 21, or 24.

An electrophoresis gel is also provided herein, where the gel includes the composition of a cyclodextrin covalently linked to at least one substituted indole moiety, in any embodiment of this composition. Also provided herein is a kit including this composition. Some embodiments of the kit also include an electrophoresis gel of which the composition is a constituent. In addition, a kit is provided that includes the electrophoresis gel mentioned above, where the gel includes the composition of a cyclodextrin covalently linked to at least one substituted indole moiety.

Another method of detecting a protein is also provided. The method includes contacting the protein with the composition of a cyclodextrin covalently linked to at least one substituted indole moiety; exposing the protein to UV light; and detecting fluorescence emission, thereby detecting the protein.

In some embodiments, the method further involves subjecting the protein to gel electrophoresis, and detecting the protein in an electrophoresis gel. In some embodiments, the protein is contacted with the composition prior to gel electrophoresis. In one such embodiment, the composition is suspended in a buffer and the contacting step includes contacting the protein with the buffer. In other embodiments, the protein is contacted with the composition subsequent to gel electrophoresis. In one such embodiment, the composition is suspended in a buffer and the electrophoresis gel is contacted with the buffer, thereby allowing the composition to diffuse into the electrophoresis gel and contacting the protein with the composition. In still other embodiments, the composition is a constituent of the electrophoresis gel, and the protein is contacted with the composition upon subjecting the protein to gel electrophoresis.

In some embodiments of the method that involve subjecting the protein to gel electrophoresis, the method further includes the steps of transferring the protein out of the electrophoresis gel and onto a blotting membrane, and detecting the protein on the blotting membrane. In one such embodiment, the method also includes removing the composition from the protein. In other such embodiments of the method, the protein includes an affinity tag or antibody-binding epitope, and detecting involves contacting the blotting membrane with a binding partner of the affinity tag or antibody-binding epitope. In some of these embodiments, the affinity tag or antibody-binding epitope includes a tryptophan residue. In one embodiment, the affinity tag is a Strep-tag.

BRIEF DESCRIPTION OF THE DRAWINGS

FIG. 2 shows fluorescent emission of proteins in SDS-PAGE gels after incubation of the gels in solutions containing 0.5% v/v trichloroethanol (TCE) and different concentrations of methyl-β-cyclodextrin (MBCD; 0, 2.5, and 25 mM).

DETAILED DESCRIPTION OF THE INVENTION

Introduction

Figure 1:
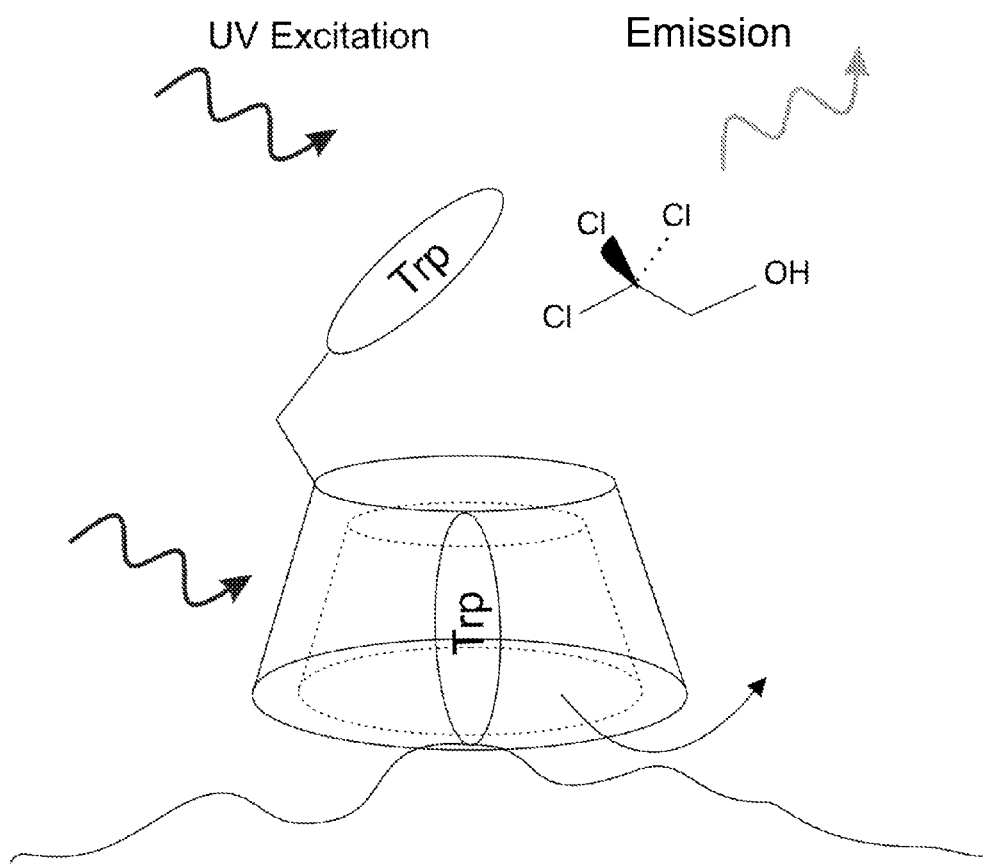
FIG. 1 shows phenomena that occur in some embodiments of the invention: UV-induced reaction of a tryptophan-labeled cyclodextrin with a halo-substituted organic compound (such as trichloroethanol), UV excitation and fluorescent emission of tryptophan-labeled cyclodextrin after reaction, sequestration of a tryptophan residue of a protein inside the cavity of the cyclodextrin, and protection of the sequestered tryptophan residue from the UV-induced reaction.

The inventors have surprisingly determined that proteins can be detected using labeled cyclodextrins. Such detection can occur without covalently modifying the amino acid sidechains of the protein being detected, to which the cyclodextrin binds. As the term is used herein, a "labeled cyclodextrin" comprises a cyclodextrin molecule covalently linked to a label. The label can include one or more indole moieties which, like tryptophan residues in standard stain-free techniques, can react with halo-substituted organic compounds upon exposure to UV light. Thus, after contacting a protein with a labeled cyclodextrin, the cyclodextrin-decorated protein can be detected using fluorescence (FIG. 1). Compared with standard stain-free techniques, the use of indole-labeled cyclodextrins can offer more sensitive protein detection because cyclodextrins can bind to phenylalanine and tyrosine residues in addition to tryptophan residues, and each cyclodextrin molecule can carry multiple indole moieties. More generally, as described below, the cyclodextrin can be covalently linked to any label that can interact with a reagent to form a detectable product. The product can be formed before or after contacting the protein with the labeled cyclodextrin. Provided herein are methods, compositions, kits, and electrophoresis gels for detecting proteins using labeled cyclodextrins.

Methods

In some embodiments, the methods involve contacting a protein with a cyclodextrin covalently linked to at least one label. Any cyclodextrin can be used in these methods, including but not limited to α-cyclodextrin, β-cyclodextrin, methyl-β-cyclodextrin, and γ-cyclodextrin. Other varieties and derivatives of cyclodextrins are known in the art (see e.g. T. Servo et al., *Advanced Drug Delivery Reviews* 63, 1086-1106, 2011). It may also be desirable to introduce chemical modifications to the cyclodextrin, apart from or in addition to the label, to improve performance of the method. Such modifications may ease attachment or detection of the label, or cause more robust binding of the cyclodextrin to a protein of interest, for example. In some embodiments, a cyclodextrin is chosen that can bind to such a protein by accommodating the side-chain of an aromatic amino acid (tryptophan, phenylalanine, or tyrosine) in its central cavity and remain associated with the protein during detection.

It will be recognized that the present methods can be adapted for use with cyclic organic host molecules other than cyclodextrins, provided these molecules can non-covalently bind selected amino acid residues of proteins and be linked to detectable labels. The host molecule generally serves to connect the protein to be detected and the label used for detection, and allows detection to occur with specificity and without covalent modification of the protein. The adaptations necessary for various embodiments of the methods will depend on the choice of host molecule, the chemistry used for linking the label to the host molecule, the conditions used for detection, attributes of target proteins of interest, and other considerations.

Any label can be used in the methods disclosed herein, provided that the label can undergo a chemical interaction with a reagent to form a detectable product, as described below. In some embodiments, the label includes an indole moiety, which can react with a halo-substituted organic compound upon exposure to UV light to form a fluorescent product. The indole moiety can be part of a tryptophan residue linked to the cyclodextrin, either as a single amino acid or as one of multiple amino acid residues within a polypeptide. Alternatively, the indole moiety can be linked to the cyclodextrin without the additional atoms that are needed to constitute a tryptophan residue, or can be part of a chemical structure that does not contain a tryptophan residue. That is, a label including an indole moiety does not necessarily include a tryptophan residue. The chemical structure that links the indole to the cyclodextrin can be chosen for ease of synthesis or for other reasons. Longer linker structures (e.g., 1, 2, 3, 4, or more glycine residues interposed between the cyclodextrin and indole) can prevent insertion of the indole into the central cavity of the cyclodextrin.

Covalently linking one or more labels to a cyclodextrin can be achieved as desired. For example, an amino acid-based label (comprising one or more amino acids, such as in an oligopeptide) can be linked to mono-amino-substituted β- or γ-cyclodextrin using DCC chemistry as described by Djedaïni-Pilard (see e.g. Djedaïni-Pilard et al., *Tetrahedron Lett.* 34, 2457-2460, 1993, and Djedaïni-Pilard et al., *J. Chem. Soc. Perkin Trans.* 2, 723-730, 1995). Here, the site of the linkage is the 6 position of one of the glucopyranose units. In unmodified cyclodextrins, a reactive primary hydroxyl group is joined to glucopyranose ring at this position. The primary hydroxyl can be selectively activated to introduce an amino group for further reaction, or can be reacted directly with a label.

The number of labels attached per cyclodextrin can also be controlled using strategies from carbohydrate chemistry. Each glucopyranose unit contains two secondary hydroxyl groups, at the 2 and 3 positions, in addition to the primary hydroxyl at the 6 position. Accordingly, labeling reactions targeted to hydroxyl groups can result in heterogeneous product mixtures where the number of labels per cyclodextrin molecule follows a statistical distribution. The mean value or shape of this distribution can be tuned by varying reaction conditions. In some embodiments, the average number of labels per cyclodextrin is at least 1, 2, 3, 4, 5, 6, 7, 8, 12, 14, 16, 18, 21, or 24. In some embodiments, the average number of labels per glucopyranose unit, or on a particular glucopyranose unit, is 1, 2, or 3. More stringent reaction conditions (e.g. lower temperatures, shorter reaction times, or lower label stoichiometries) will result in fewer labels being linked to each cyclodextrin molecule on average. In some cases, this will result in the selective addition of labels to the primary hydroxyls at the glucopyranose 6 positions. Labels at these positions can be less prone to enter the central cavity of the cyclodextrin through intramolecular sequestration, and can therefore be preferable for leaving the central cavity available for intermolecular binding. More homogeneous product mixtures can also be obtained by blocking some of the hydroxyl groups, such as with acid-labile silyl groups, before the labeling reaction or purifying the mixture after the reaction. Purification can be performed using standard liquid chromatography, reviewed for example in *Introduction to Modern Liquid Chromatography*, $3^{rd}$ ed., New York: Wiley, 2010. In the case of hydrophobic labels, such as indole moieties or tryptophan residues, reaction or purification schemes are desirable that reduce the occurance of unattached label becoming sequestered in the cyclodextrin cavity.

The protein of interest can be contacted with the labeled cyclodextrin as desired. For example, contact can occur when both components (i.e. the protein and the cyclodextrin) are in solution, by mixing a solution containing one component with a solution containing the other. Alternatively, contact can be made when either component is disposed on a surface or within a matrix, by passing a solution containing the other component over the surface or through the matrix. Other methods of contact will be apparent to those of skill in the art. As will be discussed below, contact can also occur in conjunction with subjecting the protein to gel electrophoresis. In some cases, the experimental conditions associated with contacting the protein and labeled cyclodextrin are conducive to binding between any exposed aromatic residues of the protein and the cavity of the cyclodextrin.

In some embodiments, the methods include contacting the protein with a reagent. This contacting can also be performed as desired, using any preparation or composition of the reagent. The protein can be contacted with the reagent before or after being contacted with the labeled cyclodextrin, or at the same time. The reagent and labeled cyclodextrin can be part of the same composition, e.g. suspended in the same solution. However, since detection depends on a chemical interaction occurring between the reagent and the label on the cyclodextrin, contacting the protein with the reagent should not cause the cyclodextrin to dissociate from the protein or prevent the cyclodextrin and protein from binding. To avoid such outcomes, in some embodiments the protein is contacted with the reagent after being contacted with the labeled cyclodextrin.

The reagent can be any chemical or molecular entity, including but not limited to a small organic molecule, an inorganic molecule or ionic composition, or a biological macromolecule such as a lipid, carbohydrate, nucleic acid or protein. The reagent can have any charge, pKa, pKb, pI, or molecular weight, and can occur in any phase of matter. For the present purposes, contacting the protein with a reagent can entail subjecting the protein to an altered chemical environment, such as by changing the pH or the composition of the buffer in which the protein is suspended. The reagent can therefore also be a solution or components thereof, such as hydroxide ions, hydronium ions, or a buffering agent.

A reagent can be chosen to undergo a chemical interaction with the particular label or labels covalently linked to the cyclodextrin. As the term is used herein, "chemical interaction" should be understood broadly to encompass any interaction that can result in the formation of a detectable product. Chemical interactions can include, for example, the electrostatically or sterically mediated association between two or more species, including the binding of a protein to a substrate and any cofactors. A chemical interaction can also involve a reaction between species that results in the formation or disruption of ionic, covalent, or hydrogen bonds. In the chemical interaction between the label and reagent, additional species (e.g. reactants, catalysts, or solvent molecules) can take part and may be necessary to allow the product to form. The chemical interaction can be spontaneous and occur simply by bringing the label, reagent, and any other species into contact with each other, or can require an input of energy, for example in the form of heat, radiation, or an electric current.

In some embodiments where the label contains an indole moiety, the reagent is a halo-substituted organic compound. Any halo-substituted organic compound can be used that reacts with the indole moiety to form a fluorescent product. Halo-substituted organic compounds of particular interest are trihalo compounds, most notably trichloro compounds and those with molecular weights of 200 or less. Trihaloaliphatic alcohols, trihaloaliphatic acids, trihaloaliphatic amines, and trihaloalkanes are all useful. Specific examples are chloroform, trichloroacetic acid, trichloroacetate, trichloroethanol, and 3-bromo-1-propanol. Halo-substituted organic compounds can be used individually or in combinations, such as for example combinations of two or three such compounds in approximately equal molar proportions.

The reaction, i.e. chemical interaction, between the indole moiety and halo-substituted organic compound can be caused by exposing the two reactants to UV light. This can be performed by exposing the protein to UV light after it has been contacted with the indole-labeled cyclodextrin and the halo-substituted organic compound, such that the cyclodextrin is bound to the protein and the halo-substituted organic compound remains within the chemical environment of the protein. Useful wavelengths will generally include those that reside within the range of from about 200 nm to about 400 nm. An exposure time of from about thirty seconds to about thirty minutes, or more efficiently from about one minute to about ten minutes, will generally provide adequate results. The exposure can be carried out at room temperature (70-75° F.), although higher and lower temperatures can also be used, provided that no additional or unwanted reactions occur at such temperatures, no phase changes occur, and the reaction occurs at an economically viable reaction rate. Irradiation can be achieved by transillumination, epi-illumination, or otherwise.

UV light induces the addition of an organic group derived from the halo-substituted organic compound to the indole ring, yielding a substituted indole moiety as the product of the reaction. The indole moiety thereby undergoes an increase in mass from its pre-reacted state, and this increase depends on the identity of the halo-substituted organic compound. For example, the mass increases by 28 Da per indole moiety when the compound is chloroform, 44 or 58 Da when the compound is trichloroethanol, 44 Da when the compound is trichloroacetate, and 58 Da when the compound is 3-bromo-1-propanol. These masses correspond to addition of a formyl (+28 Da), carboxylic acid (+44 Da), hydroxyethanone (+58 Da), or propanol (+58 Da) group to the indole ring (see e.g. Edwards et al., *Photochemistry & Photobiology* 75: 362-368, 2002, and Ladner et al., *Protein Science* 16: 1204-1213, 2007). An indole moiety can also increase in mass by 32 Da upon reacting with $O_2$, a process that occurs under UV irradiation and does not require the participation of a halo-substituted organic compound. Similar covalent modifications to the tryptophan residues of proteins can occur when these residues are not sequestered by cyclodextrins.

The substituted indole moiety resulting from reaction of the label is fluorescent upon further exposure to UV light and emits in the visible range. The same UV light source or wavelengths of light can be used to induce the reaction and excite the product. The protein can therefore be detected by exposing it to UV light when it is bound to a cyclodextrin that is in turn covalently linked to a substituted indole moiety. Detection can be achieved by imaging such as by the use of photography, or by electronic sensors such as photodiodes, charge-coupled device (CCD) detectors, or complementary metal-oxide semiconductor (CMOS) detectors. Digital results can be analyzed by conventional imaging software. Irradiation with excitation light for purposes of detection of emissions can be performed after the reaction has occurred, either for an initial detection or for repeat detections. Alternatively, the protein can be irradiated with UV light in one administration, to both induce the reaction and excite the product, and detection of fluorescently re-emitted light can occur at any time during this administration.

Exposure of proteins to halo-substituted organic compounds and UV light can be used to detect proteins in the absence of cyclodextrins. For example, as described in co-assigned, co-pending U.S. patent application Ser. No. 13/870,710, Stain-Free chemistry can be used to covalently modify tryptophan residues in complex protein samples (e.g., samples containing 1,000 or more distinct proteins) and render proteins in these samples fluorescent. The detected fluorescence then allows total protein quantification to be performed. The number of tryptophan residues per protein molecule can differ from one protein to the next, such that more fluorescence arises from some proteins than others. However, these differences are masked or averaged out in the complex sample, so that the total amount of measured fluorescence correlates strongly with the total amount (e.g. mass or molar quantity) of protein. Different complex samples having comparable total amounts of protein can give rise to comparable levels of fluorescence, even if the samples contain different complements of proteins.

In the present methods, cyclodextrins can also be used to perform Stain-Free total protein quantification due in part to the binding of indole-labeled cyclodextrins to tryptophan residues in proteins. As discussed above, some cyclodextrins can bind to tyrosine and phenylalanine residues as well as to tryptophan residues. Cyclodextrins can also be prepared such that more than one indole label is covalently linked to each cyclodextrin molecule on average. Thus, a cyclodextrin-decorated protein molecule can present a larger number of reactive indole moieties to the surrounding solution than a bare protein molecule having the same amino acid sequence. The decorated protein molecule can generate as much if not more fluorescence than the bare molecule upon exposure of the protein sample to a halo-substituted organic compound and UV light. For this reason, the present methods allow for highly sensitive protein detection, and can be used to perform total protein quantification in complex protein samples having small total amounts of protein.

In other embodiments of the methods disclosed herein, the label can include a biotin moiety. Biotin is a small molecule that binds with high affinity to avidin and related proteins such as streptavidin and neutravidin. Here, this binding is the chemical interaction of the method, the reagent is the protein that binds (e.g. avidin), and the detectable product is the molecular complex between biotin and the reagent. The molecular complex can be detected by methods known in the art, such as by placing a radioactive or fluorescent tag on the reagent, or by directing an antibody to the complex. Biotin-avidin is just one example of a label-reagent pairing that can be used in methods of the present invention. The choice of label is limited only by the practicalities of attaching the label to an appropriate cyclodextrin and using the labeled cyclodextrin in conjunction with a reagent to detect proteins of interest. Other possible labels include metal ions (which can interact with chelating agents) and specific amino acid sequences (e.g., affinity tags and epitopes, which can interact with specific protein binding partners).

In some embodiments, the cyclodextrin is attached to a polypeptide. The polypeptide can serve as or include the label to which the cyclodextrin is covalently linked. For example, the polypeptide can include a tryptophan residue. Alternatively, the polypeptide can be separate from the label. For example, the polypeptide can be attached to one glucopyranose unit of the cyclodextrin and an indole moiety can be linked to another glucopyranose unit. The chemistry of the polypeptide depends on its amino acid sequence, and this sequence can be chosen to modulate the solubility of the cyclodextrin. A polypeptide comprising mostly hydrophilic residues, for example, can increase the solubility of the cyclodextrin in aqueous solution, while a polypeptide comprising mostly hydrophobic residues can decrease this solubility. As a result of its solubility, the polypeptide can facilitate binding of the cyclodextrin to which it is attached to a protein of interest under desired conditions. A hydrophilic polypeptide attached to a cyclodextrin can promote binding of the cyclodextrin to a secreted protein in aqueous buffer. Similarly, a hydrophobic polypeptide attached to a cyclodextrin can promote binding of the cyclodextrin to a hydrophobic protein embedded in a membranous structure (e.g., a lipid bilayer), possibly by allowing the cyclodextrin to infiltrate this structure. If desired, the amino acid sequence can be designed to mimic the surface electrostatics of a protein of interest, as a whole or near a target aromatic side-chain where the cyclodextrin can bind. The polypeptide can have any number or sequence of amino acid residues and can be attached to the cyclodextrin as desired.

The detectable product, resulting from the chemical interaction of the label with the reagent, can take any chemical or physical form that allows detection of the protein of interest. The product can be a modified form of the label, for example a substituted indole moiety, or a molecular complex between the label and reagent, as is the case for biotin and avidin. In both of these examples, the chemical interaction between the label and reagent effectively renders the label detectable. Here, the label is incorporated into the product and the product is covalently linked to the cyclodextrin after the product is formed. Alternatively, the chemical interaction between the label and reagent can generate a product that is not linked to the cyclodextrin or protein. For example, the label can be a catalyst and the reagent can be a cleavable substrate. The label can catalyze cleavage of the reagent, thereby generating a detectable (e.g. colored) product that does not remain associated with the labeled cyclodextrin or protein after catalysis and can diffuse away. Despite this diffusion, the product can be used to detect the protein, for example on an electrophoresis gel or blotting membrane, because the protein is colocalized with the site at which the product originates. Other strategies for generating and detecting a product that is not directly linked to the labeled cyclodextrin or protein of interest are also possible.

In some embodiments, the present methods include subjecting the protein to gel electrophoresis and detecting the protein in an electrophoresis gel. Any electrophoresis gel can be used for these purposes. For example, the gel can be of any dimensions, have any number of lanes, and be prepared (poured) by hand or by machine. In some embodiments, the gel comprises polyacrylamide, which can be present at any percentage or concentration, including at more than one concentration (e.g. in stacking and resolving portions of the gel) or at a gradient of concentrations. The gel can also comprise a denaturing agent such as sodium dodecyl sulfate (SDS), as well as buffering agents such as tris(hydroxymethyl)aminomethane (Tris), glycine, or tricine. Other common constituents of electrophoresis gels, particularly gels used to separate complex protein samples, will be apparent to the skilled artisan.

In some embodiments, the gel includes additives that allow proteins to migrate through the gel faster and at higher applied voltages than would be practicable in the absence of these additives. The additives also improve separation of proteins by preventing the duplication of bands, which can result from gaps or undesired interactions between the gel and the plates between which it is held (see e.g. U.S. Pat. No. 7,056,426). Examples of such additives include poly(vinyl alcohol), agarose, poly(vinyl pyrrolidone), poly(ethylene glycol), poly (ethylene oxide), poly(propylene glycol), poly(propylene glycol)/poly(ethylene glycol) copolymers, and linear polyacrylamide. Electrophoresis gels containing one or more of these additives are available from Bio-Rad under the name 'TGX'.

The electrophoresis gel can be run using any techniques desired, and using any available materials or apparatus. In standard practice, the gel is contacted with an electrolyte-containing buffer and placed between two electrodes, and a current is applied between the electrodes. Running, or electrophoresis, causes proteins to migrate within the gel and become separated from each other according to molecular weight, size, or charge. Electrophoresis can also separate proteins from contaminants that may have been loaded onto the gel along with the proteins. Such contaminants can fail to enter the gel when the current is applied, can diffuse from the gel into the surrounding buffer, or can pass through the gel more slowly or quickly than proteins of interest. For convenience and if desired, a molecular weight marker can be loaded into the gel along with a protein sample, allowing the practitioner to track the positions of proteins in the sample during or after migration. Gel electrophoresis techniques are reviewed, for example, in Sambrook and Russell, *Molecular Cloning: A Laboratory Manual* ($3^{rd}$ ed.), New York: Cold Spring Harbor Laboratory Press, 2001.

In general, a protein of interest can be contacted with the labeled cyclodextrin and reagent however desired and practicable when subjecting the protein to gel electrophoresis. In some embodiments, for example, after running the gel, the gel can be immersed in a solution of the labeled cyclodextrin, reagent, or both. The choice of solvent and the concentration of the labeled cyclodextrin or reagent in the solution can vary widely and can readily be optimized in terms of the intensity of the signal that is ultimately produced. Any solvent or combination of solvents that will dissolve the labeled cyclodextrin or reagent can be used. Water or mixtures of water and a lower-molecular weight alcohol such as methanol, ethanol, or isopropanol, will suffice in many cases. Prolonged incubation or agitation of the gel in this solution allows the labeled cyclodextrin and/or reagent to diffuse into the gel and come into contact with proteins suspended therein. Here, the duration of incubation or agitation can be optimized empirically, keeping in mind that longer durations also allow more extensive diffusion of proteins within the gel and from the gel into solution.

Following immersion, the gel can be rinsed to remove excess labeled cyclodextrin or reagent. If the solution contained one of these two elements (labeled cyclodextrin or reagent) but not both, the process can be repeated with a solution containing the other element. Once the protein has been contacted with both elements, the reagent can be caused to undergo a chemical interaction with the label linked to the cyclodextrin, and the resulting product can be detected, as described above.

In other embodiments, the labeled cyclodextrin and/or reagent is added to the gel when it is poured, so that the labeled cyclodextrin and/or reagent is a constituent of the gel. Proteins thus come into contact with the labeled cyclodextrin or reagent during electrophoresis. When the reagent is a halo-substituted organic compound, effective and efficient results can generally be obtained with about 0.2% to about 2.0% of the halo-substituted compound in the gel, and in many cases from about 0.1% to about 0.5%, by volume. If only one of the two elements (labeled cyclodextrin or reagent) with which the protein must be contacted is present in the gel initially, the remaining element can be added by immersing the gel in an appropriate solution after electrophoresis, as described above.

The protein can alternatively be contacted with the labeled cyclodextrin, and optionally the reagent, prior to subjecting the protein to gel electrophoresis. For example, the protein, labeled cyclodextrin, and reagent can be mixed together in a buffer, so that labeled cyclodextrin can bind to the protein and undergo a chemical interaction with the reagent. After this interaction has occurred, the protein, now linked to a detectable label, can be run on the gel. The buffer can be chosen to optimize interaction among the protein, labeled cyclodextrin, and reagent, or can be chosen to optimize performance of gel electrophoresis. In some embodiments, the buffer is an aqueous solution and can be Laemmli buffer, which includes Tris-HCl, glycerol, SDS, bromophenol blue, and optionally β-mercaptoethanol. By way of another example, the protein can be bound to the cyclodextrin before being loaded and run on the gel, and then be contacted with the reagent while the gel is running or afterward, as described above. A skilled artisan will recognize that the labeled cyclodextrin and protein may not remain associated during electrophoresis, depending on the compositions of the running buffer and gel used in electrophoresis, and the chemical properties of the cyclodextrin and label, among other factors. Furthermore, association between the labeled cyclodextrin and protein can alter the migration rate of the protein through the gel.

The methods herein further provide for transferring the protein of interest out of an electrophoresis gel and then detecting it. Transfer can be accomplished using electroblotting. In some embodiments, detection is then performed using an amino acid sequence within the protein that can be recognized with high affinity and specificity by a binding partner. Such a sequence is called a recognition sequence herein. In some embodiments, the recognition sequence contains aromatic amino acid residues that can be protected from covalent modification by associating with cyclodextrins.

Electroblotting involves the transfer of proteins out of an electrophoresis gel after the gel has been run, by applying an electric field to the gel in a direction orthogonal to that used for running. The transferred proteins are deposited onto the surface of a membrane (also called a 'blot' or 'blotting membrane'; typically made of nitrocellulose or polyvinylidene fluoride (PVDF)), which is then incubated in a solution containing the binding partner. Binding between the recognition sequence and binding partner can be detected optically, for example using fluorescence or chemiluminescence, with radioactivity, or with other means known in the art.

If the recognition sequence takes an antibody as its binding partner, then the recognition sequence is termed an antibody-binding epitope or simply an epitope. Examples of epitopes commonly used in biotechnology are the FLAG and myc epitopes. A protein deposited on a blot can be detected using an antibody directed to an epitope of the protein, in a well-known technique called Western blotting. Detection can be accomplished, for example, by conjugating a fluorescent label to the antibody, illuminating the blot with an appropriate wavelength of light, and observing light re-emitted by the label. In place of the label, an appropriate enzymatic or chemical structure may be conjugated to the antibody to induce chemiluminescence. An example of such a structure is horseradish peroxidase (HRP), which catalyzes the oxidation of luminol to 3-aminophthalate in the presence of hydrogen peroxide and thereby causes visible light to be emitted. The antibody may alternatively incorporate a radioactive isotope such as 35S and be detected using a Geiger counter or photographic film sensitive to decay of the isotope.

Instead of directly detecting the antibody that binds the epitope, a secondary antibody can be used. The secondary antibody has specificity for the epitope-binding antibody (known in the art as the 'primary antibody') and can be conjugated to a fluorescent label, catalyst of chemiluminescence, or other means of detection, as described above. Following incubation of the blot with the primary antibody, the blot may be incubated with the secondary antibody, and 'sandwiched' complexes comprising the secondary antibody bound to the primary antibody bound to the epitope may be detected. Under some conditions, the blot may be stripped of bound antibodies to allow detection of proteins on the blot using a different set of antibodies.

The recognition sequence instead may bind a protein that is not an antibody, or it may bind a small molecule. In this case, the recognition sequence may be referred to as an affinity tag (although the terms 'epitope' and 'affinity tag' are sometimes used interchangeably in the art). Examples of affinity tags are STP1 (amino acid sequence WTHPQFER, SEQ ID NO: 1), Strep-TagI (amino acid sequence AWRHPQFGG, SEQ ID NO: 2), and Strep-TagII (amino acid sequence WSHPQFEK, SEQ ID NO: 3) (collectively, 'Strep-tags'), which bind the protein streptavidin and an engineered mutant thereof called Strep-Tactin (see, for example, Schmidt et al., *J. Mol. Biol.* 255, 753-766, 1996). Like antibodies (discussed above), the binding partners of affinity tags may be conjugated to appropriate molecular means of detection.

In the present methods, a protein containing a recognition sequence with aromatic amino acid residues (i.e. tryptophan, phenylalanine, or tyrosine) can be subjected to gel electrophoresis and optionally detected using a labeled cyclodextrin. For example, the protein can be contacted with a indole-labeled cyclodextrin and a halo-substituted organic compound, and the protein can be detected upon exposure to UV light. The labeled cyclodextrin can bind to aromatic residues within the protein including those within the recognition sequence. The protein can then be transferred to a blotting membrane and detected using the recognition sequence. Because the aromatic residues have been protected by the labeled cyclodextrin, they have not undergone covalent modification. In particular, tryptophan residues have not reacted with the halo-substituted organic compound. The recognition sequence therefore remains intact and competent to interact with the binding partner.

In some embodiments, chemical entities that remain from detecting the protein in the electrophoresis gel, such as the cyclodextrin, the reagent, and the detectable product, are removed from the protein prior to detecting the protein on the blotting membrane. Such removal can occur upon transferring the protein from the gel to the membrane, or can be achieved by washing the membrane after the transfer. Other removal techniques are known in the art. In other embodiments, no such removal of chemical entities is carried out or attempted. Removing the cyclodextrin, in particular, from the protein can be unnecessary when the cyclodextrin does not interfere with binding between the recognition sequence and the binding partner.

The methods described herein for detecting proteins using labeled cyclodextrins are not limited to detection on electrophoresis gels. Accordingly, proteins can be detected with labeled cyclodextrins in solution, on surfaces, or on blotting membranes, among other contexts. Detection on a blotting membrane need not make use of a recognition sequence within the protein or a binding partner for the recognition sequence, and need not be preceded by a gel electrophoresis procedure in which the protein is contacted with a cyclodextrin. Rather, for example, the protein can be subjected to electrophoresis and transferred to the blotting membrane using standard protocols. The blotting membrane, and in turn the protein, can then be contacted with a labeled cyclodextrin and reagent as described above, such as by immersing the membrane in one or more solutions. Subsequently, the product resulting from a chemical interaction between the cyclodextrin label and reagent can be detected using a technique described above or variation thereof.

The present methods also provide for directly contacting a labeled cyclodextrin with a reagent in the absence of protein. A chemical interaction can then be caused between the label covalently linked to the cyclodextrin and the reagent, rendering the label detectable. The resulting cyclodextrin can be applied directly to a protein of interest, allowing detection of the protein. Using a cyclodextrin covalently linked to an indole moiety, as well as a halo-substituted organic compound, this method can be used to prepare a cyclodextrin covalently linked to a substituted indole, which subsequently can be bound to proteins and detected upon exposure to UV light. In some embodiments, the method includes contacting a protein with a cyclodextrin covalently linked to at least one substituted indole moiety; exposing the protein to UV light; and detecting fluorescence emission, thereby detecting the protein.

Greater flexibility can be afforded if the chemical interaction rendering the label detectable occurs before contacting the protein with the labeled cyclodextrin. For example, this chemical interaction can be carried out under conditions that do not favor the cyclodextrin binding a particular protein of interest. Furthermore, detectable labeled cyclodextrin (i.e. labeled cyclodextrin that has undergone the chemical interaction) can be separated from impurities, such as undetectable labeled cyclodextrin, unlabeled cyclodextrin, or free reagent. Such separation can reduce background when detecting proteins and can be performed using chromatography or other standard techniques. However, carrying out the chemical interaction before contacting the labeled cyclodextrin with the protein can also complicate use of detectable products that do not remain linked to the cyclodextrin after formation. One example of such a product, discussed above, is a colored molecule resulting from cleavage of the reagent, where cleavage is catalyzed by the label. Such a product can diffuse away from the cyclodextrin before the cyclodextrin is bound to a protein of interest, with the result that the product and protein are not necessarily colocalized.

A cyclodextrin covalently linked to at least one detectable label, e.g. a fluorescent substituted indole moiety, can be contacted with a protein of interest as desired. For example and without limitation, contact can occur in solution, in an electrophoresis gel, or on a blotting membrane. If the protein is subjected to gel electrophoresis, contact can occur before, during, or after electrophoresis, and the detectable labeled cyclodextrin can be part of a composition with which the protein or gel is contacted, or a constituent of the gel, as discussed above. Prior to being contacted with the protein, a labeled cyclodextrin can be prepared and then caused to undergo a chemical interaction with an appropriate reagent as desired. For example, the method for causing the chemical interaction can be the same as that used when the labeled cyclodextrin and reagent are in the presence of a protein, or can be optimized around the absence of protein.

Compositions

Compositions for use in detecting proteins are also provided. The compositions can include a cyclodextrin covalently linked to at least one label, and a reagent that undergoes a chemical interaction with the at least one label, thereby rendering the label detectable. A composition can alternatively include a cyclodextrin covalently linked to at least one label, such as a substituted indole moiety, wherein the chemical interaction with a reagent has already occurred. The cyclodextrin, label, and reagent can have any of the various characteristics or identities discussed above and can be used in the methods discussed above or variations thereof. In compositions that include both a cyclodextrin and a reagent, the cyclodextrin and reagent can be held in separate containers or spaces, or can be in the same container or space (e.g. mixed together). The compositions can take any form of matter, e.g. solid or liquid. In addition to the cyclodextrin and reagent, the compositions can include other elements, such as (without limitation) solvents, matrices, catalysts, chemically reactive species, or inert substances.

Electrophoresis Gels

In some embodiments, the present application provides electrophoresis gels (also referred to herein and in the art simply as 'gels') for separating and/or detecting proteins. An electrophoresis gel as contemplated herein can include a cyclodextrin covalently linked to at least one label. The gel can also include a reagent that can undergo a chemical interaction with the at least one label, as described above. In some aspects, the gel can include a composition as described above.

The cyclodextrin, label, linkage between the cyclodextrin and label, reagent, composition, and electrophoresis gel can have any of the various characteristics or identities discussed above, and can be used in the methods discussed above or variations thereof.

The electrophoresis gel can be provided with constituents such as the labeled cyclodextrin or reagent already incorporated therein. Alternatively, the gel can be provided with means for incorporating these constituents therein. For example, precursor chemicals such as acrylamide can be provided along with the labeled cyclodextrin or reagent, so that the practitioner can incorporate these constituents into the gel upon pouring it. In another example, the labeled cyclodextrin or reagent can be provided in the form of one or more solutions along with a pre-poured gel, so that the constituents can be incorporated into the gel upon incubating the gel in the solutions. In general, the gel can be prepared using the methods described herein or known in the art.

Kits

Kits for use in detecting proteins are also provided. A kit as contemplated herein can include a cyclodextrin covalently linked to at least one label. The kit can also include a reagent that can undergo a chemical interaction with the at least one label, as described above. In some aspects, the kit can include a composition as described above. In some aspects, the kit can include an electrophoresis gel as described above, which can optionally comprise the cyclodextrin or reagent. The kit can also include an aqueous buffer, and the cyclodextrin, reagent, or other component of the kit can be a constituent of the aqueous buffer.

As they pertain to kits, the cyclodextrin, label, linkage between the cyclodextrin and label, reagent, composition, electrophoresis gel, and aqueous buffer, if any, can have any of the various characteristics or identities discussed above. The kits can be used in the methods discussed above or variations thereof.

In some embodiments, some or all components of the kit are provided in separate containers or spaces, and can be combined by the practitioner in carrying out methods to detect proteins. Combining components can include, for example, mixing together the components, incorporating one into another, or allowing one to react or interact with another. In other embodiments, some or all components of the kit are held in the same container or space and are combined before being provided to the practitioner.

EXAMPLE 1

Broad Range Standard proteins (Bio-Rad Cat. No. 161-0317) were diluted from stock to a concentration of 30 ng/µl and loaded into three TGX SDS-PAGE gels (Bio-Rad Cat. No. 456-8093). In each gel, one lane was loaded with 300 ng protein, one lane was loaded with 150 ng, and one lane was loaded with 75 ng protein. Following electrophoresis, the gels were soaked for 20 minutes in solutions containing trichloroethanol (TCE) and different concentrations of methyl-β-cyclodextrin (MBCD): (A) No MBCD+0.5% TCE v/v, (B) 2.5 mM MBCD+0.5% TCE v/v, and (C) 25 mM MBCD+0.5% TCE v/v.

Figure 3:
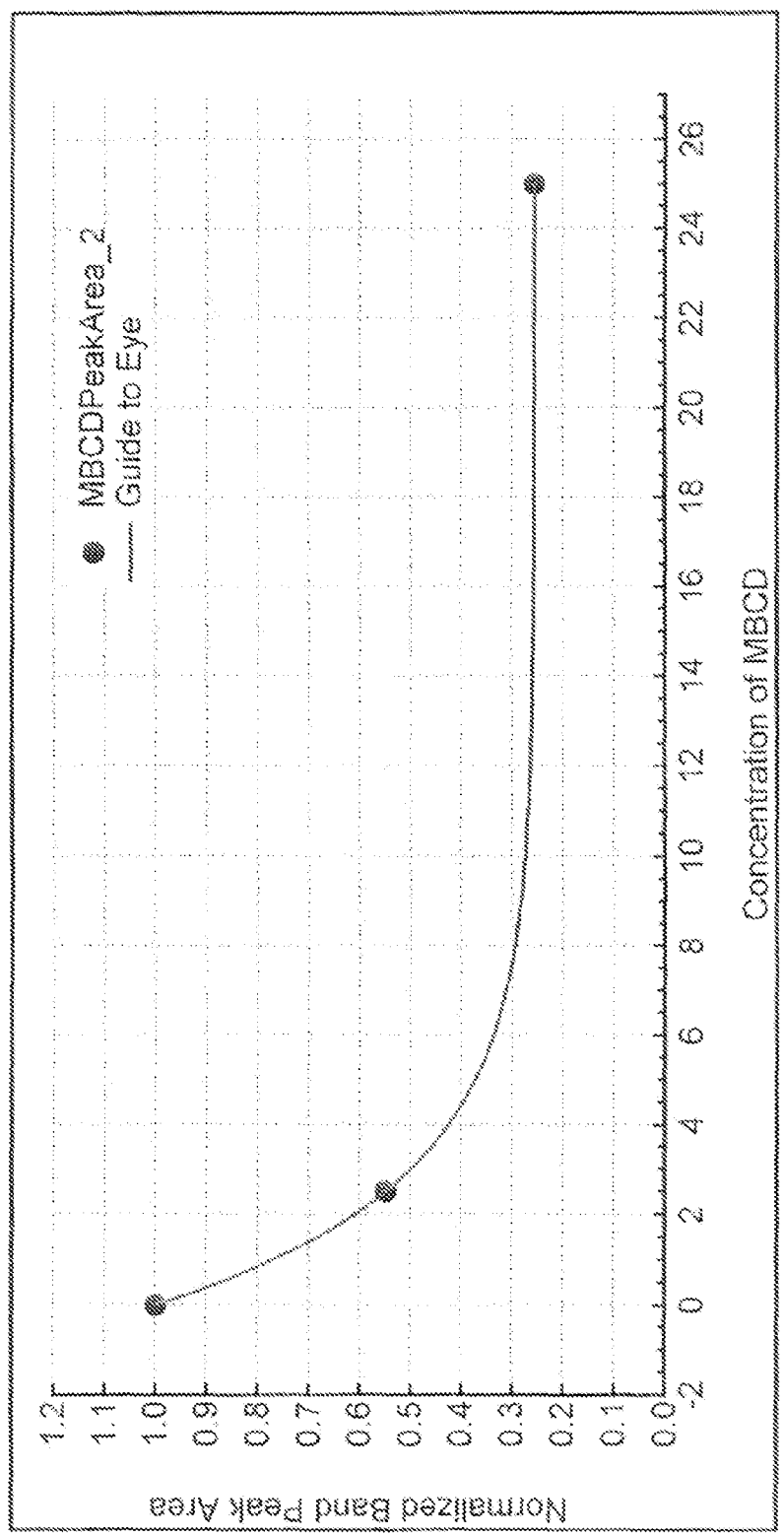
FIG. 3 shows quantitation of the ~200,000 Da bands in lanes of the SDS-PAGE gels of FIG. 2.

The gels were then exposed to UV light to allow reaction of TCE with exposed tryptophan residues and fluorescence excitation of tryptophan residues so reacted. Images of the gels, showing emitted visible light, are shown in FIG. 2. From the images, the beta-galactosidase bands (MW ~200,000 Da) in the 300 ng lanes of the gels were quantitated with standard image analysis software. The results of the quantitation are shown in FIG. 3. For both the beta-galactosidase bands and the gels as a whole, the level of detected fluorescence emission decreased as the concentration of MBCD increased. This trend indicated that tryptophan residues within the proteins were protected from reaction with TCE and covalent modification more extensively as the concentration of MBCD increased.

EXAMPLE 2

Four different concentrations of Broad Range Standard proteins were prepared by serial dilution. The four concentrations were loaded into lanes 1-4 of each of three 10% T, 2.6% C hand-poured polyacrylamide gels. Following electrophoresis, the gels were soaked in solutions containing no MBCD and varying concentrations of TCE: (A) 0.5% TCE v/v, (B) 0.47% TCE v/v, and (C) 0.25% TCE v/v. The gels were then imaged as in Example 1.

Figure 4:
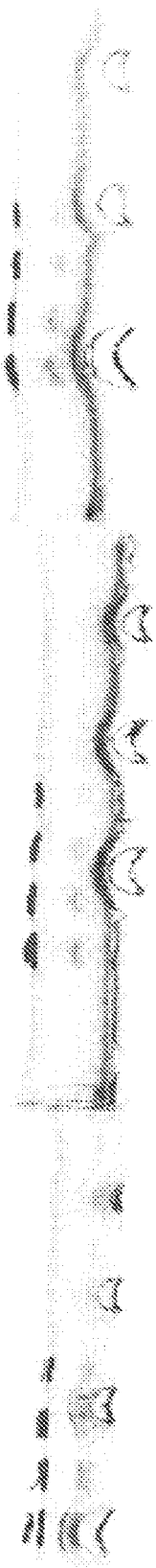
FIG. 4 shows fluorescent emission of proteins in SDS-PAGE gels after incubation of the gels in solutions containing MBCD and different concentrations of TCE (0.5, 0.47, and 0.25% v/v).

The detected fluorescence did not significantly decrease as the concentration of TCE fell (FIG. 4), indicating that the loss of signal demonstrated in Example 1 was not the result of depletion of TCE in the solution containing MBCD (via incorporation of TCE into the MBCD cavity).

* * *

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of detecting a protein, the method comprising:
   contacting the protein with a cyclodextrin covalently linked to at least one label;
   contacting the label with a reagent;
   causing the reagent to undergo a chemical interaction with the at least one label to form a product;
   detecting the product, thereby detecting the protein.

2. The method of claim 1, wherein the cyclodextrin is selected from the group consisting of α-cyclodextrin, β-cyclodextrin, methyl-β-cyclodextrin, and γ-cyclodextrin.

3. The method of claim 1, wherein the at least one label comprises an indole moiety.

4. The method of claim 3, wherein the at least one label comprises a tryptophan residue.

5. The method of claim 3, wherein the at least one label does not comprise a tryptophan residue.

6. The method of claim 1, wherein the reagent is a halo-substituted organic compound.

7. The method of claim 6, wherein the halo-substituted organic compound is selected from the group consisting of chloroform, trichloroethanol, trichloroacetate, and 3 bromo 1 propanol.

8. The method of claim 1, wherein said causing comprises exposing the protein to UV light and the product comprises a substituted indole moiety.

9. The method of claim 8, wherein the substituted indole moiety comprises a formyl, carboxylic acid, hydroxyethanone, or propanol group.

10. The method of claim 1, wherein detecting the product comprises detecting emitted light.

11. The method of claim 1, wherein the at least one label comprises a biotin moiety.

12. The method of claim 1, wherein the reagent comprises a protein selected from the group consisting of avidin, streptavidin, and neutravidin.

13. The method of claim 1, further comprising subjecting the protein to gel electrophoresis, and wherein the protein is detected in an electrophoresis gel.

14. The method of claim 13, wherein the protein is contacted with the cyclodextrin and the reagent prior to gel electrophoresis.

15. The method of claim 13, wherein the protein is contacted with the cyclodextrin and the reagent subsequent to gel electrophoresis.

16. The method of claim 15, wherein the cyclodextrin and reagent are suspended in a buffer and the electrophoresis gel is contacted with said buffer, thereby allowing the cyclodextrin and reagent to diffuse into the electrophoresis gel and contacting the protein with the cyclodextrin and reagent.

17. The method of claim 13, wherein the cyclodextrin or reagent is a constituent of the electrophoresis gel, and the protein is contacted with the cyclodextrin or the reagent upon subjecting the protein to gel electrophoresis.

18. The method of any one of claims 13, further comprising:
   transferring the protein out of the electrophoresis gel and onto a blotting membrane; and
   detecting the protein on the blotting membrane.

19. The method of claim 18, wherein the protein comprises an affinity tag or antibody-binding epitope, and detecting the protein on the blotting membrane comprises contacting the blotting membrane with a binding partner of the affinity tag or antibody-binding epitope.

20. The method of claim 19, wherein the affinity tag or antibody-binding epitope comprises a tryptophan residue.

* * * * *